US005562110A

United States Patent [19]
Ottenbrite et al.

[11] Patent Number: 5,562,110
[45] Date of Patent: Oct. 8, 1996

[54] HAIR STRAIGHTENING AND PERMANENT WAVING COMPOSITION

[75] Inventors: Rapheal M. Ottenbrite, Midlothian; Natalye Fadeeva, Richmond, both of Va.

[73] Assignee: Virginia Commonwealth University, Richmond, Va.

[21] Appl. No.: 296,932

[22] Filed: Aug. 31, 1994

[51] Int. Cl.$^6$ .................................................. A61K 7/09
[52] U.S. Cl. ........................... 132/202; 424/70.2; 132/204
[58] Field of Search .................................... 132/202, 203, 132/204, 205, 206; 424/70.2, 70.4, 70.5, 70.51

[56] References Cited

U.S. PATENT DOCUMENTS

| | | |
|---|---|---|
| 3,582,259 | 6/1971 | Kalopissis et al. .................... 424/70.2 |
| 3,583,408 | 6/1971 | Wall et al. . |
| 3,800,809 | 4/1974 | Saad et al. .............................. 132/202 |
| 4,659,566 | 4/1987 | Petrow . |
| 4,848,377 | 7/1989 | Bires et al. ............................. 132/222 |
| 5,147,634 | 9/1992 | Deshpande et al. . |
| 5,148,822 | 9/1992 | Akhtar . |
| 5,294,230 | 3/1994 | Wu et al. . |
| 5,338,540 | 8/1994 | Lee et al. . |
| 5,352,443 | 10/1994 | Kubo et al. . |

OTHER PUBLICATIONS

Cannell, D. W., "Permanent Waving and Hair Straightening," *Clinics in Dermatology*, 6(3), pp. 71–82, 1988.
Robbins, C. R., "Chemical and Physical Behavior of Human Hair," Springer Verlag, 1988.
Hamburger, W. J., et al., "Some Aspects of the Mechanical Behavior of Hair," *Proc. Sci. Sect. T.G.A. No. 14*, pp. 10–16 (Dec. 1950).
Gumprecht, J. G., et al., "Effectiveness of Reduction and Oxidation in Acid and Alkaline Permanent Waving," *J. Soc. Cosmet, Chem*. 28: 717–732, 1977.
Wolfram, L. J., et al., "The Mechanism of Hair Bleaching," *J. Soc. Cosmet. Chem*. 28: 875–900, 1970.
Leduc, M., et al., "The Buffering Capacity of Various Kinds of Hair Measurement in vitro," Hair Research, Orfanos, Montagna, Stuttgen, eds., Springer Verlag, 1981.

*Primary Examiner*—John G. Weiss
*Attorney, Agent, or Firm*—Benesch, Friedlander, Coplan & Aronoff

[57] ABSTRACT

A composition for permanently straightening and/or waving hair comprises 10–25 weight percent sodium bisulfite, 10–25 weight percent urea, and 0.1–10 weight percent morpholine. The composition is applied in a primarily aqueous solution at near neutral pH (5–8) and at tepid temperatures (35°–55°C.) for a period of time ranging between 10 and 30 minutes.

7 Claims, 2 Drawing Sheets

HAIR STRAIGHTENING AND PERMANENT WAVING COMPOSITION

BACKGROUND OF THE INVENTION

1. Field of the Invention

This invention is generally related to a composition useful for straightening hair or providing a permanent wave in hair and, more particularly, to a composition which can safely and effectively straighten or permanently wave virgin (not previously treated) Afro-American hair.

2. Description of the Prior Art

Most commercially available formulations for straightening or waving "Afro-American" or "Black" hair utilize harsh hydroxide chemicals (sodium, potassium, calcium and lithium hydroxides). The highly alkaline conditions (pH 12–14) of these products cause hair swelling and disruption of disulfide bonds followed by the formation of carbon-sulfur bonds. The high pH of the products causes the partial dissolution of the intercellular matrix in the hair cuticle, rendering the hair brittle and fragile. Under the conditions of pH 12–14, some hydrolysis of the polypeptide chains in the hair protein can also occur. Prolonged exposure of hair to a strong alkali weakens and can eventually dissolve the hair.

U.S. Pat. No. 5,148,822 to Akhtar et al. discloses a hair treatment method employed with traditional high alkaline relaxers. Rather than washing the relaxer from the hair with an "acid wash" (shampoo or rinse of acidic pH used to neutralize the relaxer), Akhtar et al. disclose adding a texturing or strengthening agent, preferably a quaternary ammonium derivative of hydrolyzed collagen protein, to the hair which has a pH between 8 and 11. The treatment method is said to enhance and sustain the cation receptivity of alkali-treated hair while shampoo resistant benefits are provided. Akhtar et al. list morpholine as an exemplary lower alkyl organic base which can be used to adjust the pH of the composition which includes the texturing and strengthening agent. No particular benefits with regard to hair straightening attributable to morpholine are disclosed.

U.S. Pat. No. 3,583,408 to Wall discloses treating hair with both a reducing agent and a vinylic monomer containing acid groups. The vinylic monomer is polymerized via addition-type polymerization during the process. The long chain polymers formed in the hair from the vinylic monomer provide a chemical backbone for strengthening the hair. The Wall patent also discloses the use of sodium bisulfite as a reducing agent responsible for breaking the disulfide bonds between the keratin molecules of the hair, and the use of urea as a swelling agent to enhance the penetration of the active ingredients into the hair fibers. Wall suggests having the sodium bisulfite constitute 1.5 to 10 percent by weight of the waving lotion.

SUMMARY OF THE INVENTION

It is an object of this invention to provide a safe and effective composition for permanent hair straightening and/or waving of the hair and, in particular, for use with virgin Afro-American hair.

According to the invention, compositions containing sodium bisulfite (10–25 wt %), morpholine (0.1–10 wt %), and urea (10–25 wt %) as principle ingredients, along with an optional use of additional ingredients such as surfactants, emulsion stabilizers, hair softening and conditioning agents, and the like, can straighten virgin Afro-American hair at tepid temperatures (35°–55° C.) and near neutral or weakly acidic pH (5–8) within a short period of time (10–30 minutes) without the use of rollers or a hot comb.

BRIEF DESCRIPTION OF THE DRAWINGS

The foregoing and other objects, aspects and advantages will be better understood from the following detailed description of the preferred embodiments of the invention with reference to the drawings, in which:

FIGS. 1a–f are pictorial views of virgin Black hair treated with different weight percentages of urea at a constant concentration of sodium bisulfite (15 wt %) which demonstrate that the formulation with less than 15 wt % each of sodium bisulfite and urea are not as effective in straightening virgin Black hair under the experimental conditions used (30 min. at 55° C.) wherein FIG. 1a shows a sample of untreated virgin Black hair, FIG. 1b shows a sample of virgin Black hair treated with a composition comprised of 15 by weight sodium bisulfite, FIG. 1c shows a sample of virgin Black hair treated with a composition comprised of 15% by weight sodium bisulfite and 10% by weight urea, FIG. 1d shows a sample of virgin Black hair treated with a composition comprised of 15% by weight sodium bisulfite and 15% by weight urea, FIG. 1e shows a sample of virgin Black hair treated with a composition comprised of 15% by weight sodium bisulfite and 20% by weight urea, and FIG. 1f shows a sample of virgin Black hair treated with a composition comprised of 15% by weight sodium bisulfite and 25% by weight urea;

FIGS. 2a–f are pictorial view of virgin Black hair treated with different weight percentages of sodium bisulfite at a constant concentration of urea (15 wt %) which also demonstrate that formulation with less than 15 wt % each of sodium bisulfite and urea are not as effective in straightening virgin Black hair under the experimental conditions used (30 min. at 55° C.) wherein FIG. 2a shows a sample of untreated virgin Black hair, FIG. 2b shows a sample of virgin Black hair treated with a composition comprised of 15% by weight urea, FIG. 2c shows a sample of virgin Black hair treated with a composition comprised of 15% by weight urea and 10% by weight sodium bisulfite, FIG. 2d shows a sample of virgin Black hair treated with a composition comprised of 15% by weight urea and 15% by weight sodium bisulfite, FIG. 2e shows a sample of virgin Black hair treated with a composition comprised of 15% by weight urea and 20% by weight sodium bisulfite, and FIG. 2f shows a sample of virgin Black hair treated with a composition comprised of 15% by weight urea and 25% by weight sodium bisulfite;

DETAILED DESCRIPTION OF THE PREFERRED EMBODIMENTS OF THE INVENTION

A composition which effectively and safely straightens or waves hair, including virgin Afro-American hair, European hair, etc., includes sodium bisulfite, urea, and morpholine as three major ingredients. Two of the major ingredients, sodium bisulfite and urea, are present in an aqueous hair straightening/waving formulation at concentrations ranging between 10 wt % and 25 wt %, while the third major ingredient, morpholine, is included at the concentration of 0.1 wt % to 10 wt %. Optionally, suitable surfactants (e.g., wetting agents, soaps, detergents, etc.), thickening agents (i.e., emulsifying agents and gel forming agents), emulsion stabilizers, hair softening and conditioning agents, as well as other agents which promote straightening (e.g., KI and other reducing agents), and other agents which are well known for use in hair straightening can be combined in the composition.

The composition, having a near neutral or weakly acidic pH (5–8), is applied to clean (shampooed) hair. The composition is left on the hair with periodic warming at tepid temperatures (35°–55° C.) for 3–5 minutes, followed by combing the hair. The warming and combing procedure is repeated 2–5 times, within a total period of treatment of 10–30 minutes, depending on the hair texture and degree of straightening desired. Waving is achieved by using curlers or other hair-deforming tools. After the desired affect is achieved, the composition is washed from the hair with comfortably warm tap water. Optionally, the hair can be shampooed and/or conditioned after the tap water rinse.

Figure 1A:
Figure 1B:
Figure 1C:
Figure 1D:
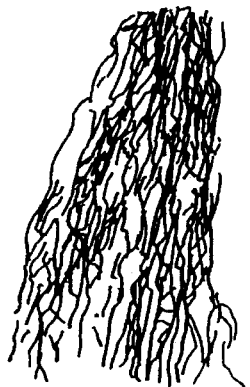
Figure 1E:
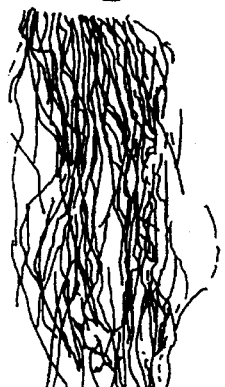
Figure 1F:
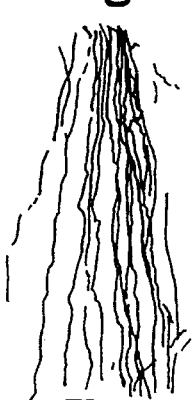
Figure 2A:
Figure 2B:
Figure 2C:
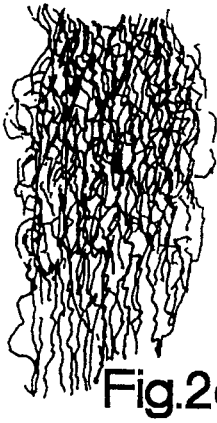
Figure 2D:
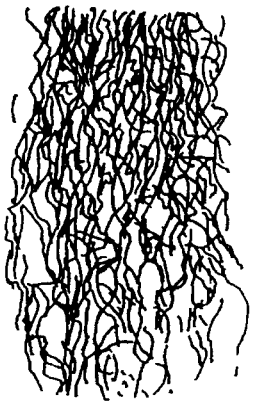
Figure 2E:
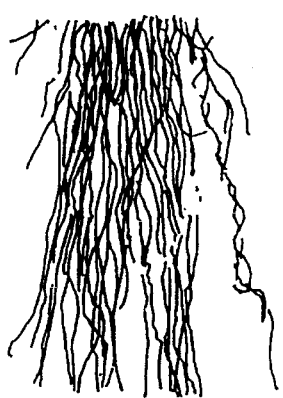
Figure 2F:
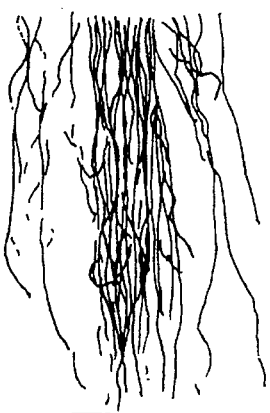

Experiments have shown that formulations with less than 15 wt % sodium bisulfite and/or 15 wt % urea were not as effective in straightening virgin Afro-American hair, and the compositions which included only sodium bisulfite and urea were much less effective than those including sodium bisulfite, urea, and morpholine. Specifically, FIGS. 1a–f and FIGS. 2a–f clearly show that significant hair straightening effects are only observed when at least 15 wt % each of sodium bisulfite and urea are used.

Figure 3A:
FIGS. 3a–f are pictorial vies of (a) untreated virgin Black hair, (b) virgin Black hair treated with a 15 wt % urea solution, (c) virgin Black hair treated with 15 wt % sodium bisulfite ($NaHSO_3$), (d) virgin Black hair treated with a composition containing 15 wt % $NaHSO_3$ and 15 wt % urea, (e) virgin Black hair treated with a composition containing 15 wt % $NaHSO_3$ and 15 wt % morpholine, and (f) virgin Black hair treated with a composition containing 15 wt % $NaHSO_3$, 15 wt % urea, and 3 wt % morpholine, respectively, at treatment conditions of 15 min. at 50° C.
Figure 3B:
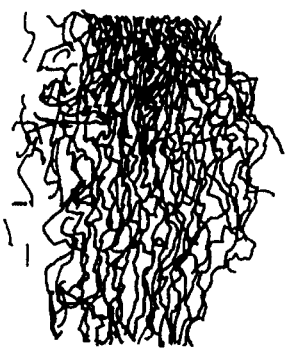
Figure 3C:
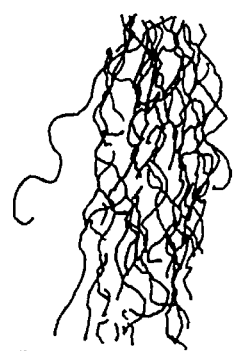
Figure 3D:
Figure 3E:
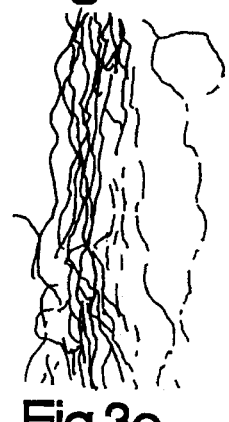
Figure 3F:
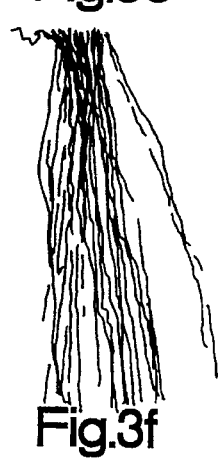

FIGS. 3a–f demonstrate the synergistic effect of sodium bisulfite, urea and morpholine. Note particularly FIGS. 3e and 3f where the addition of 3 wt % morpholine to the hair straightening formulation had a significant impact on straightening virgin Black hair.

Figure 4A:
FIGS. 4a–e are pictorial view of (a) virgin Black hair, (b) virgin Black hair treated with 15 wt % urea, (c) virgin Black hair treated with 15 wt % $NaHSO_3$, (d) virgin Black hair treated with 15 wt % $NaHSO_3$ and 15 wt % urea, and (e) virgin Black hair treated with 15 wt % $NaHSO_3$, 15 wt % urea, and 5wt % morpholine; respectively, at treatment conditions of 20 min at 45° C.
Figure 4B:
Figure 4C:
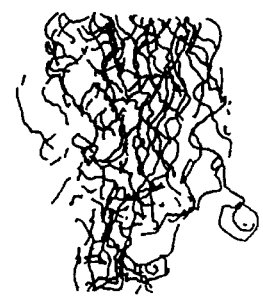
Figure 4D:
Figure 4E:

FIGS. 4a–e demonstrate that combining morpholine with urea and sodium bisulfite in the hair straightening formulation allows lower temperatures and shorter treatment times to be used in straightening virgin Black hair. Note particularly FIGS. 4d and 4e where including 5 wt % in the formulation allowed hair straightening to be achieved at 45° C.–50° C. within 15–20 minutes. By contrast higher temperatures (55° C.) and longer treatment times (30 min.) are required when morpholine is not included in the formulation.

Sodium bisulfite and urea can damage hair if they are applied at high concentrations and left in contact with the hair for prolonged times (over 30 minutes), particularly at higher temperatures (over 40° C.). Optimum results are obtained when the concentrations for sodium bisulfite and urea range between 10 wt % and 25 wt % of the formulation actually applied to the hair, and the hair is warmed at 35°–55° C. for 10–30 minutes. As discussed above, including morpholine in the formulation provides a synergistic effect, resulting in obtaining better straightening results at lower temperatures and within shorter time periods. Optimum results are obtained at morpholine concentrations ranging from 0.1 wt % to 10 wt % of the formulation actually applied to the hair. The hair should be periodically combed and warmed to 35–55° C. for 10–30 minutes prior to rinsing the sodium bisulfite/urea/morpholine combination from the hair.

Because the sodium bisulfite/urea/morpholine combination performs well at tepid temperatures (35°–55° C.) and near neutral to slightly acidic conditions (pH 5–8), the formulation can be supplied in concentrated form to be diluted in the home or at the beauty salon to the optimum sodium bisulfite, urea, and morpholine concentrations by mixing with warm water from the user's water faucet.

While the invention has been described in terms of its preferred embodiments, those skilled in the art will recognize that the invention can be practiced with modification within the spirit and scope of the appended claims.

We claim:

1. A composition for permanently straightening and/or waving hair, comprising greater than 10 weight percent sodium bisulfite, greater than 10 weight percent urea, and greater than 0.1 weight percent morpholine in an aqueous solution at a pH ranging between 5 and 8.

2. The composition of claim 1 wherein said sodium bisulfite has a concentration ranging between 10 and 25 percent by weight, said urea has a concentration ranging between 10 and 25 percent by weight, and said morpholine has a concentration ranging between 0.1 and 10 percent by weight.

3. The composition of claim 2 wherein said aqueous solution has a temperature ranging between 35° C. and 55° C.

4. A method for permanently straightening and/or waving hair, comprising the steps of:

applying to hair an aqueous solution comprising 10–25 weight percent sodium bisulfite, 10–25 weight percent urea, and 0.1–10 weight percent morpholine, said aqueous solution having a pH ranging between 5 and 8;

keeping said aqueous solution on said hair for a time interval sufficient to straighten or wave said hair;

warming said aqueous solution to a temperature ranging between 35° C. and 55° ;

combing said hair; and rinsing said aqueous solution from said hair after said time interval.

5. The method of claim 4 further comprising the step of shampooing said hair prior to said step of applying.

6. The method of claim 4 wherein said steps of warming and combing are performed several times periodically during said step of keeping said aqueous solution on said hair for a time interval sufficient to straighten or wave said hair.

7. The method of claim 6 wherein said time interval is 10–30 minutes.

\* \* \* \* \*